United States Patent
Freishtat et al.

(10) Patent No.: US 9,861,642 B2
(45) Date of Patent: *Jan. 9, 2018

(54) METHODS FOR DIAGNOSING AND TREATING ASTHMA

(71) Applicant: The Children's Research Institute, Washington, DC (US)

(72) Inventors: Robert J. Freishtat, Potomac, MD (US); Eric P. Hoffman, Kensington, MD (US)

(73) Assignee: The Children's Research Institute, Washington, DC (US)

(*) Notice: Subject to any disclaimer, the term of this patent is extended or adjusted under 35 U.S.C. 154(b) by 0 days.

This patent is subject to a terminal disclaimer.

(21) Appl. No.: 14/883,163

(22) Filed: Oct. 14, 2015

(65) Prior Publication Data

US 2016/0136182 A1 May 19, 2016

Related U.S. Application Data

(63) Continuation of application No. 13/081,218, filed on Apr. 6, 2011, now Pat. No. 9,188,581.

(60) Provisional application No. 61/321,441, filed on Apr. 6, 2010.

(51) Int. Cl.
| | |
|---|---|
| G01N 33/50 | (2006.01) |
| A61K 31/573 | (2006.01) |
| H04N 5/76 | (2006.01) |
| H04N 5/765 | (2006.01) |
| H04N 21/432 | (2011.01) |
| H04N 21/433 | (2011.01) |
| H04N 21/4335 | (2011.01) |
| H04N 21/436 | (2011.01) |
| H04N 21/442 | (2011.01) |
| H04N 21/462 | (2011.01) |
| A61K 9/00 | (2006.01) |
| A61K 31/366 | (2006.01) |

(52) U.S. Cl.
CPC .......... *A61K 31/573* (2013.01); *A61K 9/007* (2013.01); *A61K 31/366* (2013.01); *G01N 33/5023* (2013.01); *G01N 33/5044* (2013.01); *G01N 33/5064* (2013.01); *G01N 33/5091* (2013.01); *H04N 5/76* (2013.01); *H04N 5/765* (2013.01); *H04N 21/4325* (2013.01); *H04N 21/4334* (2013.01); *H04N 21/4335* (2013.01); *H04N 21/43615* (2013.01); *H04N 21/4424* (2013.01); *H04N 21/4622* (2013.01); *G01N 2800/52* (2013.01)

(58) Field of Classification Search
CPC .............. G01N 33/5064; G01N 33/5091
See application file for complete search history.

(56) References Cited

U.S. PATENT DOCUMENTS

| | | |
|---|---|---|
| 3,282,791 A | 11/1966 | Macek |
| 3,938,038 A | 2/1976 | Campbell |
| 4,021,117 A | 5/1977 | Gohde et al. |
| 6,143,560 A | 11/2000 | Imamura et al. |
| 7,537,906 B2 | 5/2009 | Nomura et al. |
| 7,763,603 B2 | 7/2010 | Tyeryar et al. |
| 8,466,185 B2 | 6/2013 | Berggren et al. |
| 9,188,581 B2 * | 11/2015 | Freishtat ............ A61K 31/4025 |
| 2003/0104358 A1 | 6/2003 | Polansky |
| 2007/0264681 A1 | 11/2007 | Hancock et al. |
| 2008/0161404 A1 | 7/2008 | Carroll et al. |
| 2010/0100977 A1 | 4/2010 | Miyawaki et al. |
| 2011/0063602 A1 | 3/2011 | Pittaro et al. |

FOREIGN PATENT DOCUMENTS

WO     2011127170 A2     10/2011

OTHER PUBLICATIONS

Hothersall et al., Thorax 63, 1070-75 (2008).*
Wark et al., Cochrane Database of Systematic Reviews 3, CD001108 (2003).*
Palmieri et al., Bone Marrow Transplantation 32, 847-48 (2003).*
Balsalobre, A. et al., Resetting of Circadian Time in Peripheral Tissues by Glucocorticoid Signaling, Science, 289, 2344-2347, 2002.
Barnes, P., Pathophysiology of Asthma, Br J Clin Pharmacol, 42, 3-10, 1996.
Bleecker, E. et al., Evidence for Multiple Genetic Susceptibility Loci for Asthma, Am J Respir Crit Care Med, 156, S113-S116, 1997.
Borish, L. et al., Interleukin-10 Regulation in Normal Subjects and Patients with Asthma, MD Consult, 97(6), 1-13, 1996.
Bucchieri, F. et al., Asthmatic Bronchial Epithelium is More Susceptible to Oxidant-Induced Apoptosis, Am J Respir Cell Mol Biol, 27, 179-185, 2002.
Busse, W. et al., Future Research Directions in Asthma, Am J Respir Crit Care Med, 170, 683-690, 2004.
Busse, W. et al., The Inhaled Steroid Treatment as Regular Therapy in Early Asthma (START) Study 5-Year Follow-Up: Effectiveness of Early Intervention with Budesonide in Mild Persistent Asthma, J Allergy Clin Immunol, 121(5), 1167-1174, 2008.
Cheng, D. et al., Airway Epithelium Controls Lung Inflammation and Injury through the NF-Kb Pathway, J Immunol, 178, 6504-6513, 2007.
Cohen, L. et al., Epithelial Cell Proliferation Contributes to Airway Remodeling in Severe Asthma, Am J Respir Crit Care Med, 176, 138-145, 2007.

(Continued)

*Primary Examiner* — Theodore R. West
(74) *Attorney, Agent, or Firm* — Dennis A. Bennett

(57) ABSTRACT

The present invention relates to asthma. Particularly, the present invention relates to clinical screening, diagnosis, prognosis, therapy and prophylaxis, as well as for drug screening and drug development for the treatment of asthma. The present invention relates to a new paradigm in diagnosing, screening, and treating asthma by affecting airway epithelial synchronization.

3 Claims, 8 Drawing Sheets

(56) References Cited

OTHER PUBLICATIONS

Cookson, W., The Alliance of Genes and Environment in Asthma and Allergy, Nature, 402, B5-B11, 1999.
Cookson, W. et al., Genetics of Asthma and Allergic Disease, Human Molecular Genetics, 9(16), 2359-2364, 2000.
Davies, D. et al., Asthma: The Importance of Epithelial Mesenchymal Communication in Pathogenesis Inflammation and the Airway Epithelium in Asthma, Int J Biochemistry and Cell Biology, 34, 1520-1526, 2002.
Davies, D. et al., Airway Remodeling in Asthma: New Insights, J Allergy Clin Immunol, 111(2), 1-17, 2003.
Fedorov, IA et al., Epithelial Stress and Structural Remodelling in Childhood Asthma, Thorax, 60, 389-394, 2005.
Freishtat, R. et al., Delineation of a Gene Network Underlying the Pulmonary Response to Oxidative Stress in Asthma, J Investigative Med, 57(7), 756-764, 2009.
Freishtat, R. et al., Glucocorticoid Efficacy in Asthma: Is Improved Tissue Remodeling Upstream of Anti-inflammation, J Investigative Med, 58(1), 1-9, Jan. 2010.
Freishtat, R. et al., Asthmatic Bronchial Epithelium is Intrinsically Inflammogenic, Mitotically Dyssynchronous, and is Rescued by Glucocorticoids, Am J Respir Crit Care Med, 181, Conference Abstract No. A2491, May 2010.
Freishtat, R. et al., Asthmatic Airway Epithelium is Intrinsically Inflammatory and Mitotically Dyssynchronous, Am J Respir Cell Mol Biol, 44, 863-869, 2011.
Gibbs, JE et al., Circadian Timing in the Lung; A Specific Role for Bronchiolar Epithelial Cells, Endocrinology, 150(1), 268-276, 2009.
Grissell, T. et al., Interleukin-10 Gene Expression in Acute Virus-Induced Asthma, Am J Respir Crit Care Med, 172, 133-439, 2005.
Guilbert, T. et al., Long-Term Inhaled Corticosteroids in Preschool Children at High Risk for Asthma, The New England Journal of Medicine, 354(19), 1985-1997, 2006.
Hammad, H. et al., Dendritic Cells and Epithelial Cells: Linking Innate and Adaptive Immunity in Asthma, Nature Reviews/Immunology, 8, 193-204, 2008.
Holgate, S., The Airway Epithelium is Central to the Pathogenesis of Asthma, Allergology International, 57(1), 1-10, 2008.
Holloway, JW et al., The Genetic Basis of Atopic Asthma, Clinical and Experimental Allergy, 29, 1023-1032, 1999.
Hostettler, KE et al., Airway Epithelium-Derived Transforming Growth Factor-B is a Regulator of Fibroblast Proliferation in Both Fibrotic and Normal Subjects, Clinical and Experimental Allergy, 38, 1309-1317, 2008.
Justice, J. Paul et al., IL-10 Gene Knockout Attenuates Allergen-Induced Airway Hyperresponsiveness in C57BL/6 Mice, Am J Physiol Lung Cell Mol Physiol, 280, L363-L368, 2001.
Kauffmann, F. et al., Epidemiologic Study of the Genetics and Environment of Asthma, Bronchial Hyperresponsiveness, and Atopy, Chest, 121(3) Supplement, 27S, 2002.
Knutsson, U. et al., Circadian Cortisol Rhythms in Healthy Boys and Girls: Relationship with Age, Growth, Body Composition, and Pubertal Development, Journal of Clinical Endocrinology and Metabolism, 82(2), 536-540, 1997.
Koppleman, GH et al., Genetic and Environment in Asthma: The Answer of Twin Studies, Eur Respir J, 13, 2-4, 1999.
Lang, D., New Asthma Guidelines Emphasize Control, Regular Monitoring, Cleveland Clinic Journal of Medicine, 75 (9), 641-653, 2008.
Larj, M. et al., Therapeutic Responses in Asthma and COPD, Chest, 126(2) Supplement, 138S-149S, 2004.
Lemanske, R., Asthma Therapies Revisited, Proc Am Thorac Soc, 6, 312-315, 2009.
Makela, MJ et al., IL-10 is Necessary for the Expression of Airway Hyperresponsiveness but Not Pulmonary inflammation After Allergic Sensitization, PNAS, 97(11), 6007-6012, 2000.

Makinde, T. et al., The Regulatory Role of TGF-b in Airway Remodeling in Asthma, Immunology and Cell Biology, 85, 348-356, 2007.
Malavia, N., et al., Airway Epithelium Stimulates Smooth Muscle Proliferation, Am J Respir Cell Mol Biol, 41, 297-304, 2009.
Message, S. et al., Rhinovirus-Induced Lower Respiratory Illness is Increased in Asthma and Related to Virus Load and Th1/2 Cytokine and IL-10 Production, PNAS, 105(36), 13562-13567, 2008.
Murray, C. et al., Secondary Prevention of Asthma by the Use of Inhaled Fluticasone Propionate in Wheezy Infants (IFWIN): Double-Blind, Randomised, Controlled Study, The Lancet, 368(9537), 754-762, 2006.
Parker, J. et al., A 3-D Well-Differentiated Model of Pediatric Bronchial Epithelium Demonstrates Unstimulated Morphological Differences Between Asthmatic and Nonasthmatic Cells, Pediatric Research, 67(1), 17-22, 2010.
PCT Application No. PCT/US2011/031418, International Search Report, Dec. 26, 2011.
PCT Application No. PCT/US2011/031418, IPRP, Oct. 9, 2012.
Perng, D. et al., Leukotriene C4 Induces TGF-B1 Production in Airway Epithelium via p38 Kinase Pathway, Am J Respir Cell Mol Biol, 34, 101-107, 2006.
Puchelle, E. et al., Airway Epithelial Repair, Regeneration, and Remodeling After Injury in Chronic Obstructive Pulmonary Disease, Proc Am Thorac Soc, 3, 726-733, 2006.
Puddicombe, S. et al., Increased Expression of p21waf Cyclin-Dependent Kinase Inhibitor in Asthmatic Bronchial Epithelium, Am J Respir Cell Mol Biol, 28, 61-68, 2003.
Rosenwasser, L., Biologic Activities of IL-1 and its Role in Human Disease, J Allergy Clin Immunol, 102(3), 344-350, 1998.
Royce, S. et al., Effect of Extracellular Matrix Composition on Airway Epithelial Cell and Fibroblast Structure: Implications for Airway Remodeling in Asthma, Annals of Allergy, Asthma & Immunology, 102, 238-246, 2009.
Shefrin, A. et al., Use of Dexamethasone and Prednisone in Acute Asthma Exacerbations in Pediatric Patients, Canadian Family Physician, 55, 704-706, 2009.
Sont, J. et al., Clinical Control and Histopathologic Outcome of Asthma when Using Airway Hyperresponsiveness as an Additional Guide to Long-Term Treatment, Am J Respir Crit Care Med, 159, 1043-1051, 1999.
Szefler, S. et al., Long-Term Effects of Budesonide or Nedocromil in Children with Asthma, The New England Journal of Medicine, 343(15), 1054-1063, 2000.
Takanaski, S. et al., Interleukin 10 Inhibits Lipopolysaccharide-Induced Survival and Cytokine Production by Human Peripheral Blood Eosinophils, J Exp Med, 180, 711-715, 1994.
Tesfaigzi, Y., Roles of Apoptosis in Airway Epithelia, Am J Respir Cell Mol Biol, 34, 537-547, 2006.
Wadsworth, S. et al., Glucocorticoids Increase Repair Potential in a Novel In Vitro Human Airway Epithelial Wounding Model, J Clin Immunol, 26(4), 376-387, 2006.
Walter, D. et al., Critical Role for IL-13 in the Development of Allergen-Induced Airway Hyperreactivity, J Immunol, 167, 4668-4675, 2001.
Weiss, S., Epidemiology and Heterogeneity of Asthma, Annals of Allergy, Asthma & Immunology, 87, 5-8, 2001.
Wersto, R. et al., Doublet Discrimination in DNA Cell-Cycle Analysis, Cytometry (Communications in Clinical Cytometry), 46, 296-306, 2001.
Wills-Karp, M., The Gene Encoding Interleukin-13: A Susceptibility Locus for Asthma and Related Traits, Respir Res, 1(1), 19-23, 2000.
Zahm, JM et al., Cell Migration and Proliferation During the In Vitro Wound Repair of the Respiratory Epithelium, Cell Motility and the Cytoskeleton, 37, 33-43, 1997.

\* cited by examiner

METHODS FOR DIAGNOSING AND TREATING ASTHMA

This application is a continuation of U.S. patent application Ser. No. 13/081,218 filed Jun. 4, 2011, which claims priority to U.S. Provisional Patent Application Ser. No. 61/321,411, filed Apr. 6, 2011, which is incorporated herein by reference.

FIELD OF THE INVENTION

The present invention relates to asthma. More particularly, the present invention relates to clinical screening, diagnosis, prognosis, therapy and prophylaxis, as well as for drug screening and drug development for the treatment of asthma.

BACKGROUND OF THE INVENTION

Asthma is a chronic inflammatory disease of the lower respiratory tract characterized by airway hyperresponsiveness and mucus obstruction (Busse et al., Am J Respir Crit Care Med 2004, 170:683-690). Bronchial asthma is the most common chronic disease affecting children and young adults and is a complex genetic disorder with several overlapping phenotypes (Cookson and Moffatt, Hum. Mol. Genet. 9: 2359-64 (2000); Weiss, Ann. Allergy Asthma Immunol., 87 (Suppl 1): 5-8 (2001)). There is strong evidence for a genetic component in asthma (Bleecker et al., Am J Respir. Crit. Care. Med., 156: S113-6 (1997); Kauffmann et al., Chest, 121(3 Suppl): 27S (2002)). Multiple environmental factors are also known to modulate the clinical expression of asthma as well as the asthma-associated phenotypes: bronchial hyperresponsiveness, atropy and elevated IgE (Koppelman et al., Eur. Resp. J, 13: 2-4 (1999); Cookson, Nature, 25: B5-11 (1999); Holloway, Clin. Exp. Allergy, 29: 1023-1032 (1999)). It is a commonly held view that asthma is caused by multiple interacting genes, some having a protective effect and others contributing to the disease pathogenesis, with each gene having its own tendency to be influenced by the environment (Koppelman et al., 1999; Cookson, 1999; Holloway, et al., 1999). Thus, the complex nature of the asthma phenotype, together with substantial locus heterogeneity and environmental influence, has made it difficult to uncover factors that underlie asthma.

Pharmacologic analogues of cortisol (e.g. prednisone) have been used clinically since 1948 and remain the standard of care for the treatment of a variety of inflammatory diseases including asthma (Larj et al., Chest 2004; 126: 138S-149S). These glucocorticoids (GC) reduce pathological inflammation that is central to asthma, and they are thought to control clinical asthma symptoms through their anti-inflammatory effects (Expert Panel Report 3 (EPR-3): Guidelines for the Diagnosis and Management of Asthma-Summary Report 2007. J Allerg y Clin Immunol 2007, 120:S94-138.). For example, Martinez and co-workers report that inhaled fluticasone shows sustained (albeit reversible) improvement in the proportion of asthma episode-free days, a reflection of reduced inflammation, compared to placebo over a two-year study period (Guilbert et al., N Engl J Med 2006, 354:1985-1997). Curiously, anti-inflammatory agents that specifically target inflammatory cells (e.g. eosinophils, T and B cells) and their intercellular signaling pathways have not shown similar efficacy to GCs in human trials (Lemanske, Proc Am Thorac Soc 2009, 6:312-315). That argues against the idea that asthmatic inflammation is merely the result of interactions between external stimuli and classic inflammatory cells like eosinophils and T cells. Rather, it is likely to involve complex interactions among multiple cell types including non-inflammatory resident cells of the lung (i.e. airway epithelium, fibroblasts, and smooth muscle).

Therefore, there remains a need for a new model of asthma and the use of that model for diagnosis, drug screening, and treating asthma.

SUMMARY OF THE INVENTION

To that end, the present inventors proposed a model for asthma placing airway epithelium at the center of a network of interacting inflammatory mediators. Due to its ability to simultaneously respond to airborne pathogens and environmental challenges and interact with its tissue environments, airway epithelium is regarded as a key lung tissue in asthma. In addition, airway epithelium communication with lamina propria fibroblasts (Davies et al., J Allergy Clin Immunol 2003; 111:215-225; quiz 226) and smooth muscle has been described (Malavia et al., Am J Respir Cell Mol Biol 2009; 41:297-304). Our model predicts that asthmatic inflammation is driven by intrinsic inflammatory, fibrogenic, and regenerative characteristics of epithelium that are rescued by GCs.

The present inventors have discovered that mitotically active asthmatic airway epithelium is asynchronous when compared to normal cells (non-asthmatic). Additionally, when those asthmatic cells are treated with a composition capable of pausing cell cycle, such as dexamethasone, the asthmatic cells become more synchronous.

Accordingly, the present invention relates to methods for diagnosing asthma. The methods comprise obtaining a cell sample of an individual's airway epithelium, inducing the cells to undergo mitosis, and determining the synchrony of the mitotic cells. Asynchronous mitosis indicates the increased likelihood of asthma. Cell synchrony of the sample is compared to that of normal cells. Generally, less than about 70 percent, preferably 65 percent, more preferably 60 percent of cells in the same phase of the cell cycle indicates asynchrony and indicates an increased susceptibility to asthma.

The present invention further provides methods for monitoring the treatment efficacy of an individual with asthma. The methods comprise administering a pharmaceutical composition to an individual, obtaining a cell sample of an individual's airway epithelium, inducing the cells to undergo mitosis, and determining the synchrony of the mitotic cells. If the cells become more synchronous upon the administration of the pharmaceutical composition, the treatment is likely effective.

The present invention further provides methods for screening for an agent capable of alleviating asthma. This method involves inducing an airway epithelium cell sample to undergo mitosis, exposing the cell sample to an agent, and determining the synchrony of the mitotic cells. If the cells become increasingly synchronous upon exposure to the agent (when compared to cells not exposed to the agent), the agent is a good candidate for further study in treating asthma.

The present invention also relates to methods for synchronizing airway epithelia by administering to the epithelia a composition capable of pausing mitosis in a particular phase of mitosis so that the cells can be synchronized. The composition preferably stops mitosis only briefly to let the cells catch up to the particular phase of mitosis. Once the cells are in phase, they can proceed through the cell cycle synchronously.

The present invention also relates to methods for treating or alleviating the symptoms of asthma in an individual by administering to the individual a composition capable of pausing mitosis in a particular phase of mitosis so that the cells can be synchronized. The composition needs to stop mitosis only briefly to let the cells catch up to the particular phase of mitosis. Once the cells are in phase, they are then allowed to proceed through the cell cycle synchronously. Thus, the composition is administered for only a short period of time (about 2 hours or less, preferably about 1 hour or less), rather than around the clock as in the current treatments of asthma which treat inflammation rather than cell synchronization.

The compositions appropriate to synchronize airway epithelia and to treat asthma include glucocorticoids, statins, azoles, and antineoplastic agents. Examples of glucocorticoids include hydrocortisone, cortisone acetate, prednisone, prednisolone, methylprednisolone, dexamethasone, betamethasone, triamcinolone, beclometasone, fludrocortisone acetate, deoxycorticosterone acetate, and aldosterone. Examples of statins include atorvastatin, cerivastatin, fluvastatin, lovastatin, mevastatin, pitavastatin, pravastatin, rosuvastatin, and simvastatin. Examples of azoles include clotrimazole, posaconazole, ravuconazole, econazole, ketoconazole, voriconazole, fluconazole, itraconazole, and carbimazole. Examples of antineoplastics include actinomycins such as dactinomycin; anthracyclines such as, doxorubicin, daunorubicin, valrubicin, idarubicin, and epirubicin; and certain antibiotics such as bleomycin, plicamycin, and mitomycin.

DETAILED DESCRIPTION OF THE PREFERRED EMBODIMENTS

Figure 1:
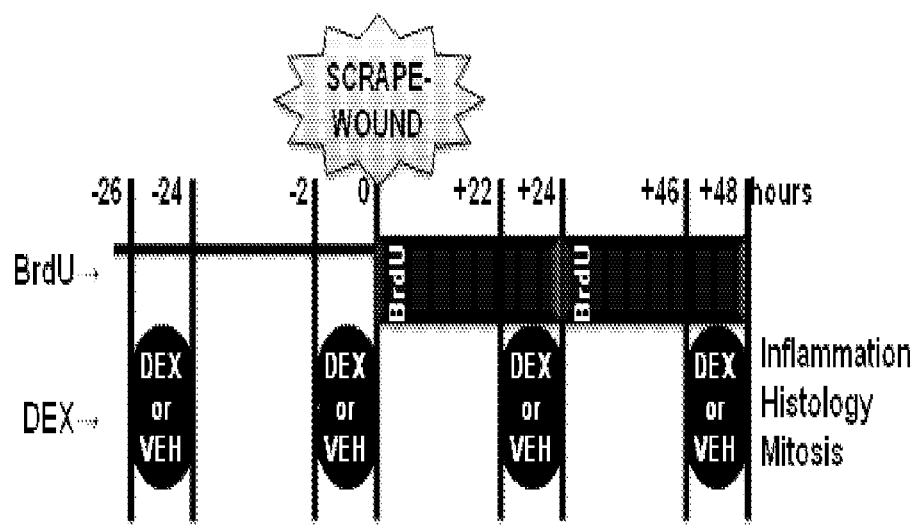
FIG. 1 is a chart that shows the experimental design for in vitro wounding of respiratory epithelia. Epithelia were pulsed for 2 h every 24 h with 20 nM dexamethasone (DEX) or vehicle (VEH) at the times shown. Mechanical scrape-wounding occurred at 0 h with continuous apical and basolateral BrdU exposure until cell harvest at +48 h for histological and mitotic analyses. Media samples were frozen before measurement of inflammatory cytokines.

The present inventors have discovered that mitotically active asthmatic airway epithelium is asynchronous when compared to normal cells (non-asthmatic). Additionally, when those asthmatic cells are treated with a composition capable of pausing cell cycle, such as dexamethasone, the asthmatic cells become more synchronous.

Methods of the present invention depend on the measure of cellular synchrony. "Synchronous," or variations thereof, as used herein, refers to a population of cells where the cells are in the same phase of the mitotic cell cycle. Conversely, "asynchronous" or "dyssynchonous" or variations thereof, as used herein refers to a population of cells where the cells are in different phases of the mitotic cell cycle. Thus, a population of cells is 60 percent synchronous when 60 percent of the cells are in the same phase of the cell cycle. That same population can also be described as 40 percent asynchronous. Cellular synchrony can be determined using methods well-known in the art as cell cycle analysis. Flow cytometers are often used for cell cycle analysis. In this measurement, the relative fraction of sample cells in the G1/G0, S, G2, or M phase of the cell cycle can be determined by staining them with a DNA-specific dye and passing them through the excitation volume of a flow cytometer. The size and amount of DNA in the nucleus of a given particle is dependent on its cell cycle stage and, hence, the pulses produced by particles in different stages have different shapes. Pulses may be analyzed according to their amplitude, area, and width using well-known techniques as described in Wersto et al. (Cytometry 46:296-306 (2001)), which is incorporated herein by reference. Alternative techniques for pulse shape analysis are described in U.S. Pat. Nos. 4,021,117 and 3,938,038, and U.S. Patent Application Publication No. 2011/0063602, which are incorporated herein by reference.

Alternatively, cell cycle analysis can be carried out using a BrdU label. That method includes: causing a BrdU to be taken into a cell for a given period; and subsequently, carrying out immunohistochemistry by using an anti-BrdU antibody. Another method for cell cycle analysis is disclosed in U.S. Patent Application Publication No. 2010/0100977, which is incorporated herein by reference.

Use of Airway Epithelium Synchrony as Diagnostics

As described herein, cellular synchrony of airway epithelia may be used as diagnostic markers for the detection, diagnosis, or prognosis of asthma. For instance, an airway epithelium sample from a patient may be assayed by any of the methods described herein, or by any other method known to those skilled in the art, for cell cycle synchrony. Asynchronous airway epithelium indicates asthmatic conditions or increased likelihood of asthma in the patient. Generally, less than about 70 percent, preferably 65 percent, more preferably 60 percent of cells in the same phase of the cell cycle indicates asynchrony and indicates an increase susceptibility to asthma.

Alternatively, the synchrony of the sample can be compared to that of a control (non-asthmatic cells). If the synchrony of the sample is less than that of the control, then asthma can be diagnosed. The diagnosis can be made by looking at airway epithelium synchrony alone or in conjunction with the other diagnostic methods known in the art, such as medical history, family history, symptoms, spirometry, methacholine challenge test, exhaled nitric oxide test, etc.

Use of Airway Epithelium Synchrony for Drug Screening

According to the present invention, airway epithelium synchrony may be used as markers to evaluate the effects of a candidate drug or agent on treating asthmatic patients.

A patient suffering from asthma is treated with a drug candidate and the progression of the disease is monitored over time by looking at his/her airway epithelium synchrony. This method comprises treating the patient with a drug candidate, periodically obtaining airway epithelium samples from the patient, determining the cellular synchrony of the samples, and comparing the synchrony over time to determine the effect of the agent on the progression of asthma. The drug candidate can be considered effective in treating asthma, if it improves cell synchrony in the patient.

Alternatively, the screening of the drug candidate can be accomplished ex vivo by using an asthmatic airway epithelia cell suspension or cell culture. Here, the cells are induced to undergo mitosis. The drug candidate is then brought into contact with the cells for a predetermined time period, preferably for less than about 4 hours, more preferably less than about 2 hours, and most preferably less than about 1 hour. More preferably, the drug candidate is administered to the cells for two periods, once within a 24 hour cycle. For example, the cells can be brought in contact with the drug candidate for 4 hours our of each 24 hour period for two periods. After that contact time, the synchrony of the cells is determined. This is then compared with a control cell population that has not been in contact with the drug candidate. If the drug candidate is able to synchronize the cells, when compared to the control, then it is a viable candidate for further testing as a drug to treat asthma.

The candidate drugs or agents of the present invention can be, but are not limited to, proteins, peptides, small molecules, vitamin derivatives, as well as carbohydrates. In addition to the proteins, DNA encoding these proteins, antibodies to these proteins, peptide fragments of these proteins or mimics of these proteins may be introduced into the patient as candidate agents. "Mimic" as used herein refers to the modification of a region or several regions of a peptide molecule to provide a structure chemically different from the parent peptide but topographically and functionally similar to the parent peptide. A skilled artisan can readily recognize that there is no limit as to the structural nature of the candidate drugs or agents of the present invention.

Use of Airway Epithelium Synchrony for Monitoring Disease Progression

Airway epithelium synchrony can also be used to monitor progression of asthma in a patient, for instance, the development of asthma. For instance, a sample from a patient may be assayed by any of the methods described herein, and the cell synchrony may be compared to the levels found in non-asthmatic individuals. The airway epithelium synchrony can be monitored over time to track progression of asthma in the patient. The present methods are especially useful in monitoring disease progression because the degree of asynchonicity is proportional to the severity of asthma. Comparison of the cell synchrony may be done by researcher or diagnostician or may be done with the aid of a computer and databases.

Treatment of Asthma by Affecting Cell Synchrony

In an embodiment, the present invention provides methods for synchronizing airway epithelia by contacting the airway epithelia with a compound or drug capable of pausing mitosis (and thereby synchronizing the epithelia). The contact of the compound or drug with the epithelia takes place over a relatively short period of time, preferably about 4 hours, more preferably about 2 hours or less, most preferably about 1 hour or less. That short contact period is sufficient to synchronize the cells. As a consequence of cellular synchronization, the airway epithelia reduces inflammatory cytokine secretion.

Cell synchrony can be used as a target for asthma treatment. Compounds or drugs that are capable of synchronizing airway epithelium can be administered to an asthmatic patient to treat, alleviate, or ameliorate symptoms of asthma. Preferably, the drug pauses mitosis in a particular phase so that the cells can be synchronized. The composition needs to stop mitosis only briefly to let the cells catch up to the particular phase of mitosis. Once the cells are in phase, the effect of the drug is no longer needed. Thus, the advantage of targeting cell synchrony, rather than inflammation, is that the drug can be used at a much lower dose because of the short time frame required to synchronize the cells. Accordingly, the dosage used is half, preferably ⅓, more preferably ¼ of the normal recommended dosage of that particular drug, which results in lower possible side and adverse effects associated with the particular drug. Alternatively, the compound or drug can be administered or compounded so that the area under the blood concentration vs. time curve (AUC) is lower than for the recommended dosage for the particular drug. Either way, the shorter exposure to the drug results in lower side effects while maintaining effectiveness.

The compounds or drugs appropriate to synchronize airway epithelia and to treat asthma include glucocorticoids, statins, azoles, and antineoplastic agents. Examples of glucocorticoids include hydrocortisone, cortisone acetate, prednisone, prednisolone, methylprednisolone, dexamethasone, betamethasone, triamcinolone, beclometasone, fludrocortisone acetate, deoxycorticosterone acetate, and aldosterone. Examples of statins include atorvastatin, cerivastatin, fluvastatin, lovastatin, mevastatin, pitavastatin, pravastatin, rosuvastatin, and simvastatin. Examples of azoles include clotrimazole, posaconazole, ravuconazole, econazole, ketoconazole, voriconazole, fluconazole, itraconazole, and carbimazole. Examples of antineoplastics include actinomycins such as dactinomycin; anthracyclines such as, doxorubicin, daunorubicin, valrubicin, idarubicin, and epirubicin; and certain antibiotics such as bleomycin, plicamycin, and mitomycin. One particular class of molecules is the compound disclosed in U.S. Patent Application Publication No. 2010/0087408, which is incorporated herein by reference.

The terms "preventing" or "treating" or "ameliorating" and similar terms used herein, include prophylaxis and full or partial treatment. The terms may also include reducing symptoms, ameliorating symptoms, reducing the severity of symptoms, reducing the incidence of the disease, or any other change in the condition of the patient, which improves the therapeutic outcome.

The administration of the drug can be through any known and acceptable route. Such routes include, but are not necessarily limited to, oral, via a mucosal membrane (e.g., nasally, via inhalation, rectally, intrauterally or intravaginally, sublingually), intravenously (e.g., intravenous bolus injection, intravenous infusion), intraperitoneally, and subcutaneously. Administering can likewise be by direct injection to a site (e.g., organ, tissue) containing a target cell (i.e., a cell to be treated). Furthermore, administering can follow any number of regimens. It thus can comprise a single dose or dosing of the drug, or multiple doses or dosings over a period of time. Accordingly, treatment can comprise repeating the administering step one or more times until a desired result is achieved. In embodiments, treating can continue for extended periods of time, such as weeks, months, or years. Those of skill in the art are fully capable of easily developing suitable dosing regimens for individuals based on known parameters in the art. The methods thus also contemplate controlling, but not necessarily eliminating, asthma. The preferred route of administration in accordance with the present invention is via inhalation.

The amount to be administered varies depending on the subject, stage of the disease, age of the subject, general health of the subject, and various other parameters known and routinely taken into consideration by those of skill in the medical arts. As a general matter, a sufficient amount of the drug will be administered in order to make a detectable change in the symptom of asthma. Suitable amounts are disclosed herein, and additional suitable amounts can be identified by those of skill in the art without undue or excessive experimentation. The dosage used in accordance with the present invention is lower than the usual recommended dosage for the particular drug as noted in the package insert, prescribing information, or the Physician's Handbook. For the present invention, the dosage used is half, preferably ⅓, more preferably ¼ of the normal recommended dosage of that particular drug. Alternatively, the drug can be administered so that the AUC is lower than for the recommended dosage.

The drug is administered in a form that is acceptable, tolerable, and effective for the subject. Numerous pharmaceutical forms and formulations for biologically active agents are known in the art, and any and all of these are contemplated by the present invention. Thus, for example, the drug can be formulated in oral solution, a caplet, a capsule, an injectable, an infusible, a suppository, a lozenge, a tablet, a cream or salve, an inhalant, and the like. It should be evident that the preferred dosage form provides for efficient contact of the drug with the airway epithelia to effect synchronization of those cells.

Without further description, it is believed that one of ordinary skill in the art can, using the preceding description and the following illustrative examples, make and use the present invention and practice the claimed methods. The following examples are given to illustrate the present invention. It should be understood that the invention is not to be limited to the specific conditions or details described in the examples.

Example 1

We proposed a model placing airway epithelium at the center of a network of interacting inflammatory mediators Our model predicts that asthmatic inflammation is driven by intrinsic inflammatory, fibrogenic, and regenerative characteristics of epithelium that are rescued by glucocorticoids.

We present herewith data that support this proposed model. We utilized a well-established in vitro system wherein human primary airway epithelial cells, lacking inflammatory cells, from normal and asthmatic individuals are differentiated at an air-liquid interface to morphologically mimic conducting airway epithelium. Our experiments showed that when induced to regenerate, asthmatic epithelium is intrinsically inflammatory, fibrogenic, and mitotically dyssynchronous. Furthermore, intermittent glucocorticoid exposures simultaneously reduced asthmatic inflammation and resynchronized epithelial mitotic regeneration.

Materials and Methods

Cell Culture and Intermittent Glucocorticoid Exposures

Normal (n=3) and asthmatic (n=6) primary differentiated human airway (i.e. bronchial) epithelia grown in 12-well plates on collagen-coated Transwell membrane inserts at an air-liquid interface were obtained commercially (#AIR-606 and #AIR-606-Asthma; MatTek Corporation, Ashland, Mass.). Donors underwent bronchoscopic brushing to acquire epithelial cells. Descriptive donor information provided by MatTek Corporation for the individuals from whom cells were obtained is shown in Table 1.

TABLE 1

Description of human bronchial epithelial cell donors*

|  | Donor Age (Years) | Gender | Race | Smoking | Medications |
|---|---|---|---|---|---|
| Asthmatic | 7 | Female | Caucasian | No | Albuterol |
|  | 9 | Female | African American | No | Albuterol, Fluticasone, Salmeterol |
|  | 27 | Female | African American | No | Unknown |
|  | 43 | Female | African American | No | Oral and inhaled steroids |
|  | 45 | Female | Caucasian | Yes | Albuterol, Fluticasone, Salmeterol |
|  | 46 | Female | Caucasian | Yes | None |
| Normal | 5 | Female | Caucasian | No | None |
|  | 13 | Male | Caucasian | No | None |
|  | 33 | Female | Caucasian | No | None |

*Provided by MatTek, Inc.

On arrival, the in vitro epithelia were washed with phosphate buffered saline (PBS) and the basal medium was replaced with proprietary defined medium supplied by the manufacturer. Cells were equilibrated at 37° C. and 5% $CO_2$ for 16 h followed by medium replacement with identical proprietary medium lacking glucocorticoids and epidermal growth factor (EGF). This condition was maintained for an additional 22 h. Upon completion (i.e. −26 h on the experimental timeline shown in FIG. 1, intermittent glucocorticoid exposures began: Dexamethasone (DEX) (20 nM) or PBS vehicle (VEH) was added to the apical and basolateral epithelial surfaces for 2 h. At −24 h, the medium was replaced with glucocorticoid- and EGF-free medium. This two-hour DEX/VEH pulse was repeated every 24 h (i.e. at −2, +22, and +46 h) thereafter until cell harvest at +48 h.

Mechanical Injury Model

An in vitro epithelial injury model that allows for the study of epithelial repair processes in the lung was adapted for use in this study. Briefly, at 0 h on the timeline in FIG. 1, epithelia were scraped in two perpendicular lines with a p1000 pipette tip and placed in bromodeoxyuridine (BrdU)-containing (10 μM) medium. BrdU-containing medium was changed at +24 h following the DEX/VEH pulse mentioned previously. Epithelia were incubated at 37° C. and 5% $CO_2$ until +48 h. In some experiments, wounds were imaged daily (i.e. 0, +24, +48 h) using a 16× phase contrast objective lens and wound area was measured in triplicate by a single operator blinded to the culture conditions using ImageJ Software (Rasband. ImageJ. Bethesda, Md., USA: U. S. National Institutes of Health; 1997-2009). Contrast was enhanced equally in all images to improve wound visualization.

Although the cultures were kept at an air-liquid interface, depending on interval culture time they generated up to 0.5 mL of apical secretions (including fluid used to wash the apical surface). These apical secretions and all basolateral media (~1 mL) were collected at all time points and frozen prior to analysis. No medium was added to the apical surface of the cultures to maintain them at an air-liquid interface.

Analysis of Inflammatory MediatorS

Inflammatory (i.e. interleukin [IL]-1β, IL-6, IL-10, and IL-13) and fibrogenic (i.e. transforming growth factor [TGF]-β1) cytokines were measured in apical and basolateral secretions at 0, +24, and +48 h by flow cytometry on a FACSCalibur™ System (BD Biosciences, San Jose, Calif.) using a FlowCytomix Multiplex Kit with FlowCytomix Pro 2.3 software (Bender MedSystems, Burlingame, Calif.). These cytokines were selected as an initial screening set for these experiments because of their prominent role in asthmatic inflammation and/or remodeling Cell Cycle Analysis Epithelia were washed once with PBS and harvested at +48 h (FIG. 1) for analysis by flow cytometry. A single cell suspension was achieved by exposure for 5 minutes with trypsin-ethylenediaminetetraacetic acid (EDTA) solution (#T3924; Sigma-Aldrich, St. Louis, Mo.) followed by filtration through a 40 μm strainer. Cells were simultaneously labeled with the following according to the manufacturers' protocols: 1) Carboxyfluorescein FLICA Apoptosis Poly-Caspase Detection Kit (Immunochemistry Technologies, LLC, Bloomington, Minn.) and 2) APC BrdU Flow Kit containing 7-AAD (amino-actinomycin-D) (BD Biosciences, San Jose, Calif.). Flow cytometry data were generated on a FACSCalibur™ System (BD Biosciences). Samples were gated to study 7-AAD content in $BrdU^+FLICA^-$ cells. Data were analyzed by means of the cell cycle analysis feature of FlowJo 7.6 (Tree Star, Inc., Ashland, Oreg.) using a Watson (Pragmatic) model with equal coefficients of variation for the G1/G0 and G2/M peaks Statistical Analysis Statistical comparisons were performed in SPSS 17.0 software (SPSS Inc., Chicago, Ill.) using T-test functions within time points. Results are reported as mean±SEM unless otherwise noted.

Results

Injured Asthmatic Epithelium is Inflammatory and Fibrogenic

Figure 2:
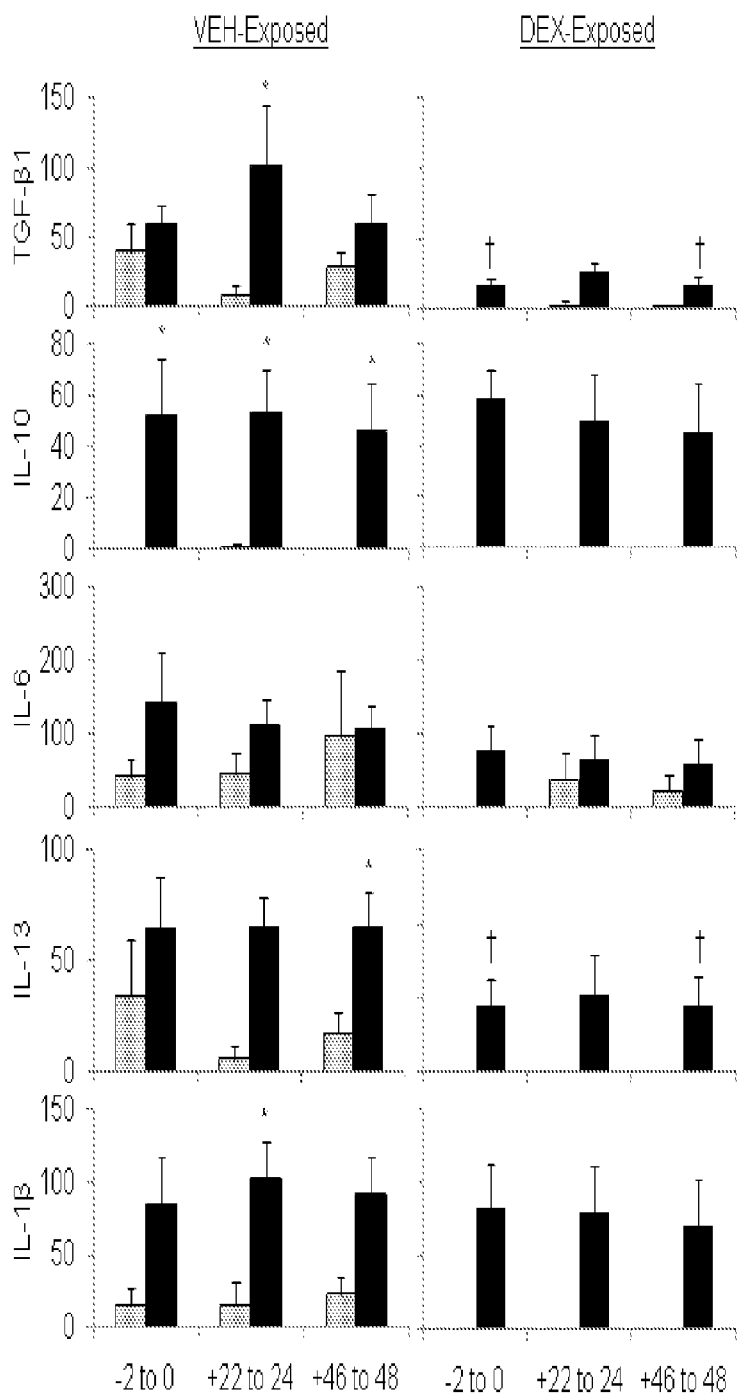
FIG. 2 is a chart that shows that asthmatic epithelial basolateral secretions are relatively inflammatory after wounding. Levels of specific cytokines (TGF-β1, IL-10, IL-6, IL-13, and IL-1β) measured by cytometric bead assay are shown for basolateral epithelial secretions from asthmatic and normal epithelia at 0, +24, and +48 h. Asthmatic epithelia had significantly higher basolateral secretion of TGF-β1, IL-10, IL-13, and IL-1β at one or more time points. DEX pulses decreased secretion of TGF-β1 and IL-13 in asthmatic epithelia. Data are shown as mean±SEM in pg/mL.

Flow cytometric bead assays were used to quantify a select screening group of inflammatory (i.e. IL-1β, IL-6, IL-10, and IL-13) and fibrogenic (i.e. TGF-β1) cytokines in apical and basolateral secretions from asthmatic and normal epithelia at 0, +24, and +48 h post-wounding. Normal and asthmatic epithelia at time 0 h (i.e. before wounding) exhibited statistically similar levels of the cytokines investigated except for higher basolateral secretion of IL-10. However, asthmatic epithelia basolaterally secreted significantly higher levels of four of the five cytokines during wound healing (FIG. 2). In particular, there was a significant between-group (i.e. asthma>normal) difference for secretion of TGF-β1, IL-10, IL-13, and IL-1β (all P<0.05) for at least one time point during wound healing (FIG. 2). IL-6 was the only cytokine for which basolateral secretion was not significantly different between asthmatic and normal epithelia.

Figure 8:
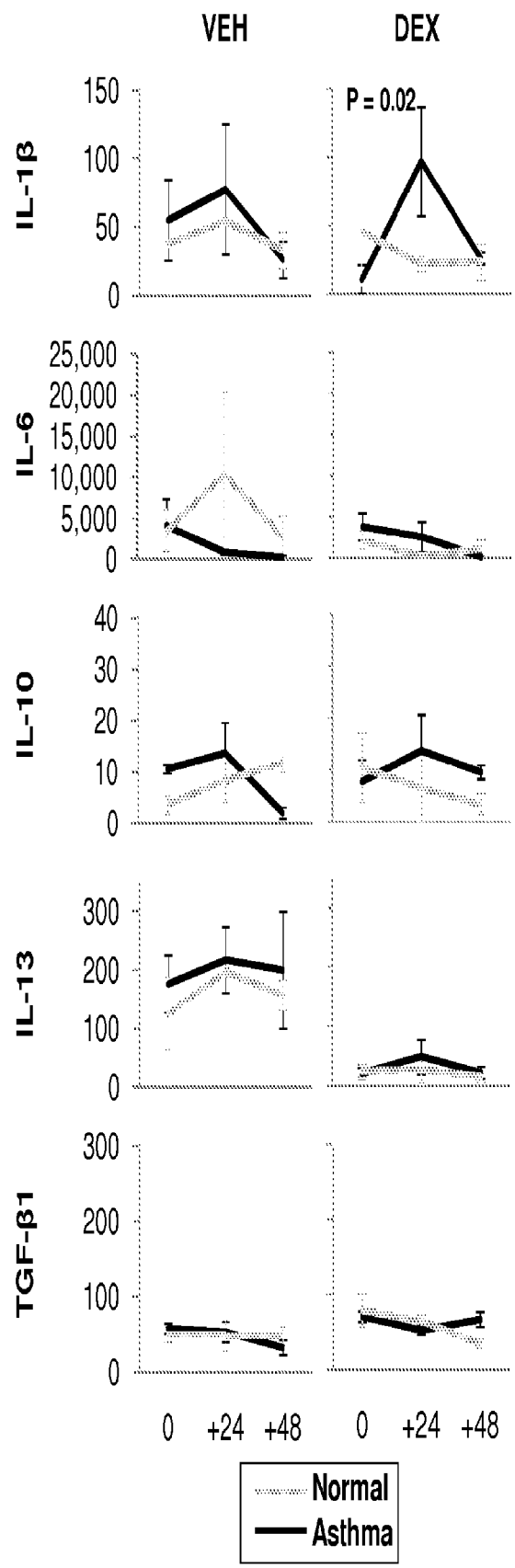
FIG. 8 is a chart that shows that asthmatic epithelial apical secretions are no more inflammatory than normals after wounding. Levels of specific cytokines (IL-1β, IL-6, IL-10, IL-13, and TGF-β1) measured by cytometric bead assay are shown for apical epithelial secretions from asthmatic and normal epithelia at 0, +24, and +48 h. Apical asthmatic epithelial cytokine secretion was not statistically significantly different from normal epithelial apical secretion. DEX-exposure decreased secretion of IL-13 in both normal and asthmatic epithelia. Levels of other measured cytokines were unchanged on DEX-exposure, except IL-1β which differed between DEX-exposed asthmatic and normal epithelia. This difference appeared only at +24 h. Data are shown as mean±SEM. Only significant (<0.05) P-values are shown for between-group comparisons (i.e. asthma versus normal) by repeated measures general linear.

With DEX pulses, asthmatic TGF-β1 and IL-13 basolateral secretion were significantly reduced. Although generally higher than in basolateral secretions, cytokine levels in apical secretions were not different between wounded untreated asthmatic and normal epithelia, except that IL-1β levels were significantly increased at 24 h in asthmatic secretions (FIG. 8).

Asthmatic Epithelial Cell Mitosis is Slow and Dyssynchronous

Figure 3:
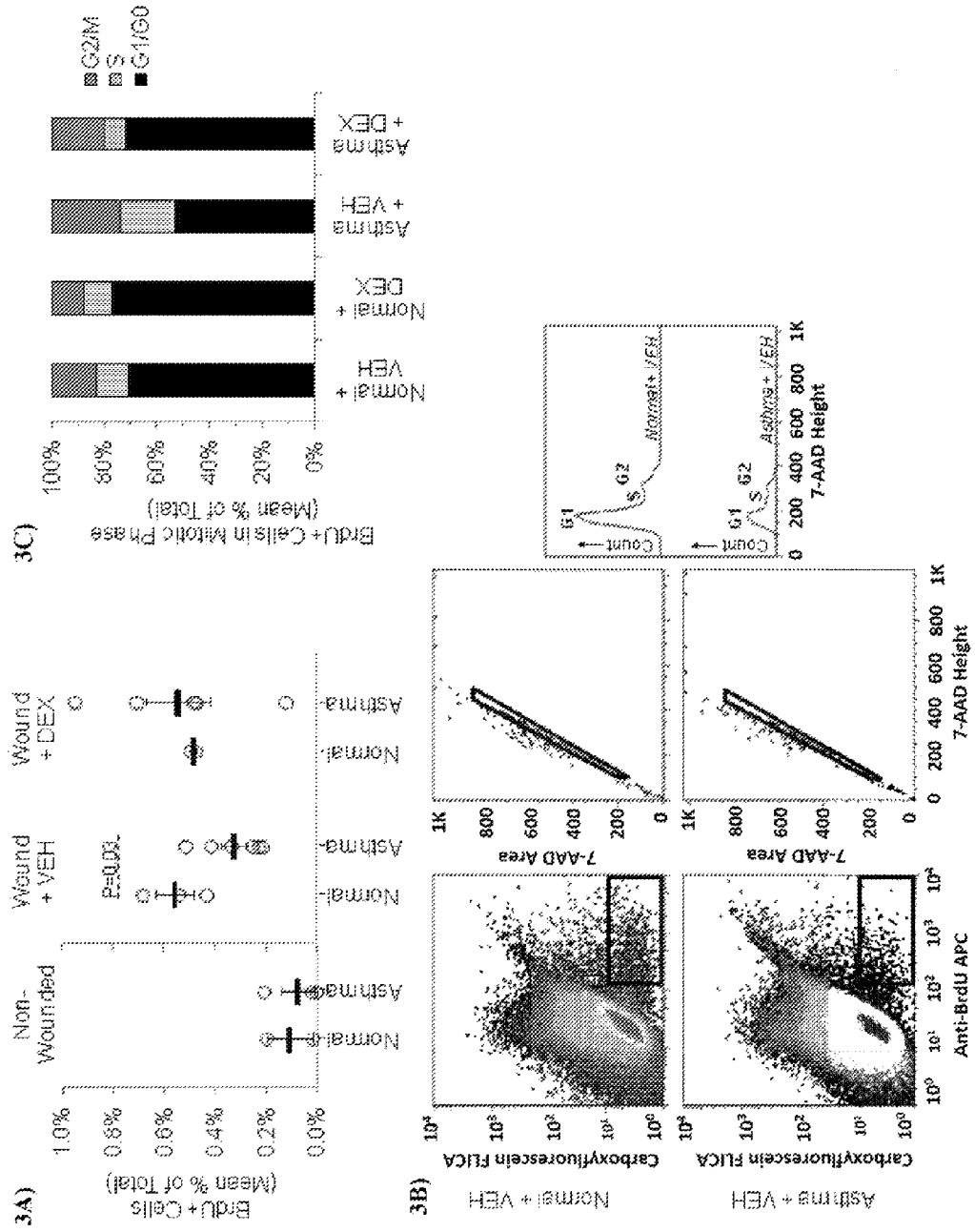
FIG. 3 is a series of charts that show that mitosis is diminished in asthmatic epithelium and increased by pulse DEX. Flow cytometry was used to measure the presence of BrdU in single cell suspensions of normal and asthmatic human airway epithelia at +48 h. A) The quantity of BrdU positivity is shown as the percent of total counted cells in non-wounded, wounded, and wounded DEX-pulsed epithelial cultures. Asthmatic epithelial wounds (n=6) showed approximately 40% fewer mitotically active cells than normal epithelial wounds (n=3) but intermittent DEX exposures abrogated this difference. B) Shown are gating and cell cycle analyses for one representative wounded normal and one representative wounded asthmatic epithelial culture. All events measured by the cytometer were gated on the BrdU+ FLICA-population (left panels). The selected cells were further gated by 7-AAD height and area to remove cell doublets (middle panels). Finally, 7-AAD height was used to identify the cell cycle distribution of the gated cell population (right panel). C) Compared to wounded normal epithelia, wounded asthmatic epithelia at +48 h showed a more even distribution of BrdU+ cells among the cell cycle phases (i.e. G1/G0, S, and G2/M) consistent with mitotic dyssynchrony. Intermittent exposures of the asthmatic epithelia to DEX improved cell cycle synchrony as shown by normalization of the percentage of mitotic cells in each cell cycle phase.

Epithelia were harvested into single cell suspensions at +48 h for flow cytometry. Non-wounded asthmatic and normal epithelia showed similar minimal background levels of BrdU$^+$ cells, an indicator of mitosis (FIG. 3A). Due to the lack of mitotic cells, no cell cycle analysis was performed on samples from this condition.

Wounded asthmatic epithelia showed 40% fewer BrdU$^+$ cells than wounded normal epithelia (mean±SEM: 0.32±0.05% vs. 0.56±0.07% of total cells; P=0.03). Exposure of normal cells to pulses of DEX did not significantly alter the quantity of BrdU$^+$ cells in normal epithelia, whereas the quantity of asthmatic epithelial mitosis approximated normal levels with DEX pulses (0.55±0.13%; P=0.19 vs. wounded untreated asthmatic cells) (FIG. 3A). In order to evaluate normal and asthmatic epithelial mitosis during wound repair, flow cytometric cell cycle analysis for DNA content (i.e. 7-AAD) was performed by gating on BrdU$^+$ cells with no detectable caspase activation (i.e. apoptosis) (FIG. 3B). Notably, caspase$^+$ (i.e. apoptotic) cells were rare in all conditions. Cells in active mitosis were presumed to be regenerating the scrape wound because of the extremely low rate of background mitosis in non-wounded cultures. As shown in FIG. 3C, normal epithelial mitosis was fairly synchronous (e.g. >70% of cells in G1/G0) in the absence and presence of pulse DEX. Conversely, mitotically-active asthmatic epithelial cells exhibited a dyssynchronous distribution among the cell cycle phases (i.e. G1/G0, S, G2/M) (53±5, 21±3, 26±4%) compared to normal epithelia (71±1, 12±2, 17±2%). DEX-pulsed asthmatic cells showed similarly synchronous mitotic activity to normal cells.

Normal and Asthmatic Epithelia Exhibit Differential Wound Healing

Figure 4:
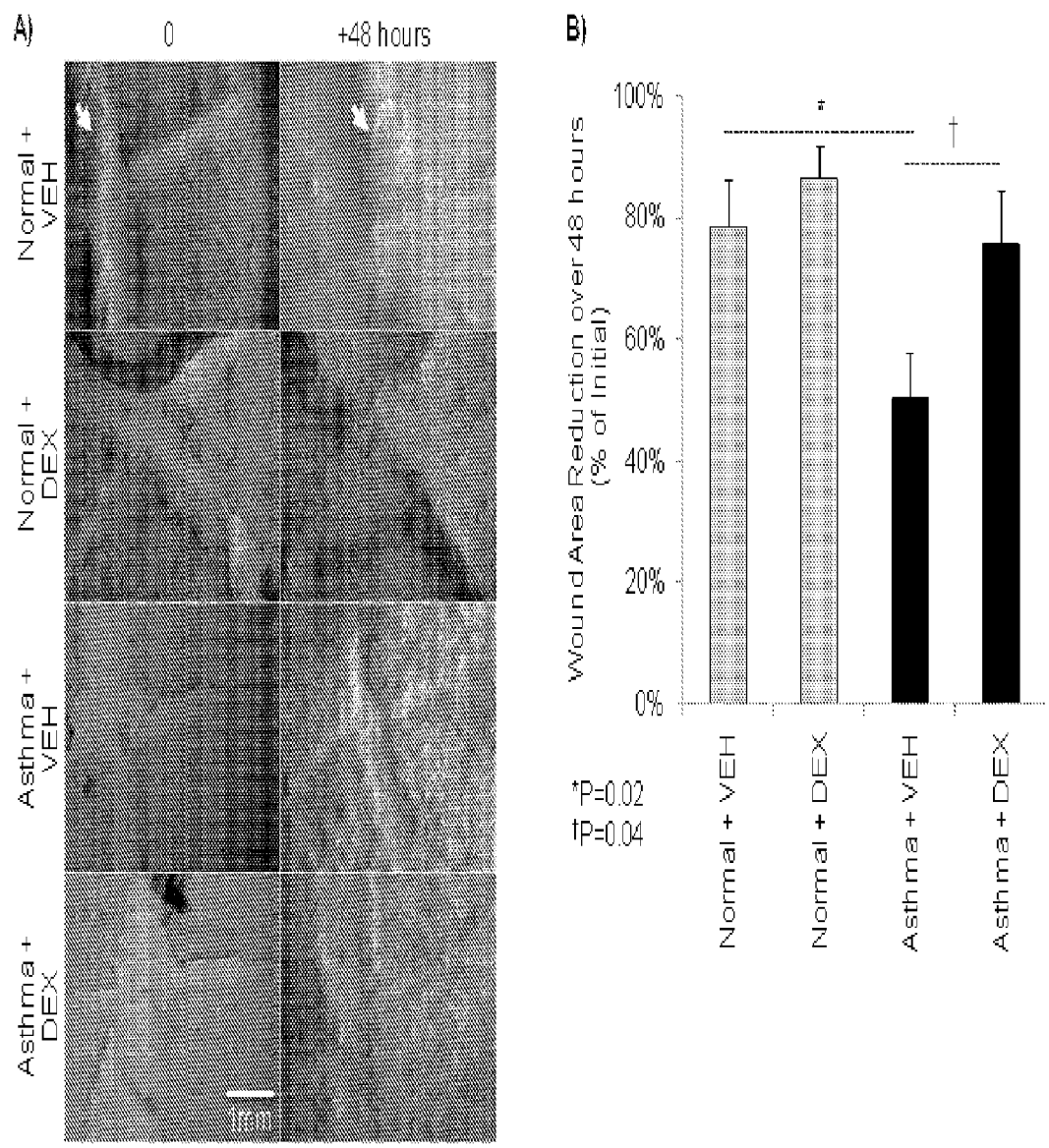
FIG. 4 are images and a chart that show that regeneration of asthmatic human airway epithelia is impaired. A) Shown are contrast-enhanced bright-field microscopy (16×) images of scrape-wounded primary differentiated human airway epithelia at wounding (i.e. 0 h) and +48 h from representative normal and asthmatic donors. Normal epithelial wounds showed complete healing in all conditions (i.e. 20 nM DEX or VEH) by +48 h. Similarly cultured asthmatic epithelia showed thinly repaired wounds at +48 h regardless of DEX exposure. [N.B. The wounds are pale appearing X-shaped regions. Thick appearing dark areas (arrows) are heaped up areas of epithelium resulting from the scraping process. B) Percent wound area reduction over 48 h according to culture condition and DEX exposure. Wound area was measured in triplicate by a single operator blinded to the culture conditions using ImageJ Software.

Wounded normal and asthmatic epithelia were imaged by bright field microscopy daily at 0, +24, and +48 h using a 16× phase contrast objective lens. As illustrated in FIG. 4A, normal epithelial wounds showed visible healing regardless of DEX pulse. Alternatively, the asthmatic scars appeared relatively thin and were still visible at +48 h regardless of DEX pulses. This was evaluated quantitatively by measurement of the wound area. Normal wound area decreased from 0 to +48 h by 78.6±7.7% with vehicle alone and 86.8±5.4% with DEX pulses. However, in the absence of DEX, asthmatic epithelial wound area decreased by significantly less (50.2±7.5%; P=0.02) than normals. With DEX pulses, asthmatic wound narrowing improved significantly (75.7±9%; P=0.04) (FIG. 4B).

Discussion

We studied cultures of human primary differentiated asthmatic and normal airway epithelia cultured at an air-liquid interface. As in a recent study (Parker et al., *Pediatr Res* 67:17-22), we found that confluent, quiescent normal and asthmatic epithelial cultures were similar with minimal secretion of cytokines and mitotic activity as evidenced by BrdU labeling. However, upon mechanical wounding, asthmatic and normal epithelia exhibited different responses. The asthmatic epithelial cultures showed increased basolateral secretion of inflammatory/fibrogenic cytokines (as exemplified by TGF-β1, IL-10, IL-13, and IL-1β) and showed slow, poorly synchronized mitosis relative to normal controls. This predictably was associated with the poor wound repair observed for asthmatic epithelia. Those markers of inflammation and dyssynchronous regeneration were attenuated by intermittent glucocorticoid-pulses. These results support our proposed model that predicts asthmatic inflammation is driven by intrinsic inflammatory, fibrogenic, and regenerative characteristics of airway epithelium that are rescued by glucocorticoids.

Cytokine (i.e. TGF-β1, IL-10, IL-13, and IL-1β) secretion in our experiments in response to epithelial injury is important given accumulating evidence for airway epithelium-induced inflammatory cell recruitment (Cheng et al., J Immunol 2007, 178:6504-6513; Hammad et al., Nat Rev Immunol 2008, 8:193-204), and proliferation of fibroblasts (Perng et al., Am J Respir Cell Mol Biol 2006, 34:101-107; Hostettler et al., Clinical & Experimental Allergy 2008, 38:1309-1317; Royce et al., Annals of Allergy, Asthma and Immunology 2009, 102:238-246) and smooth muscle (Malavia et al., Am J Respir Cell Mol Biol 2009, 41:297-304). In particular, basolateral secretion of TGF-β1, which was increased in asthmatic epithelia in our experiments, is one of the key mediators of fibroblast and smooth muscle proliferation (Makinde et al., Immunol Cell Biol 2007, 85:348-356) and is a central component of our previously published airway epithelial stress response gene/protein network (Freishtat et al., J Investig Med 2009). Further, IL-1β activates many inflammatory genes in asthma (Rosenwasser, J Allergy Clin Immunol 1998, 102:344-350) and IL-13 is a critical mediator of the classical Th2 asthmatic inflammation (Walter et al., J Immunol 2001, 167:4668-4675; Wills-Karp, Respiratory Research 2000, 1:19-23). Conversely, IL-10 is a potent immunoregulatory and anti-inflammatory cytokine that suppresses eosinophils (Takanaski et al., J Exp Med 1994; 180:711-715), decreases airway hyperresponsiveness (Makela et al., PNAS 2000, 97:6007-6012; Justice et al., Am J Physiol Lung Cell Mol Physiol 2001, 280:L363-368), and is increased during acute viral exacerbations of asthma (Grissell et al., Am J Respir Crit Care Med 2005; 172:433-439). The elevated basolateral secretion of IL-10 from asthmatic epithelium at all time points suggests a constitutive epithelial counter-regulation of inflammation in vitro. This runs counter to reports of decreased IL-10 in BAL fluid from individuals with asthma (Borish et al., The Journal of allergy and clinical immunology 1996, 97:1288-1296; Message et al., PNAS 2008, 105:13562-13567). However, this difference may be accounted for by BAL fluid cytokines reflecting both apical epithelial and inflammatory cell secretions.

In addition to inflammation, epithelial regeneration is of particular importance in asthma due to the fact that many typical asthma triggers, including tobacco smoke and viruses, are known to induce apoptotic injury in airway epithelium (Tesfaigzi et al., Am J Respir Cell Mol Biol 2006, 34:537-547). Epithelial stress/injury, independent of inflammation, has been observed in moderate and severe childhood asthma (Fedorov et al., Thorax 2005, 60:389-394). In fact, airway epithelial injury, in the forms of physical damage to the columnar cell layer and apoptosis (Cohen et al., Am J Respir Crit Care Med 2007, 176:138-145; Bucchieri et al., Am J Respir Cell Mol Biol 2002, 27:179-185), is a hallmark of asthma (Holgate, Allergol Int 2008, 57:1-10). Puchelle and colleagues have shown that regeneration of normal human airway epithelium in response to injury includes three stages: cell spreading/migration, proliferation, and differentiation (Zahm et al., Cell Motil Cytoskeleton 1997, 37:33-43; Puchelle et al., Proc Am Thorac Soc 2006, 3:726-

733). Using a similar in vitro mechanical injury model to the one used in our study, Wadsworth et al showed that normal human differentiated airway epithelial wounds closed over the initial 16 to 24 h. This primarily reflected cell migration mediated by autocrine EGF secretion that subsequently led to mitosis of epithelial cells within the wound (Wadsworth et al., J Clin Immunol 2006; 26:376-387). Our results for normal epithelium wound repair were temporally similar to those described by Wadsworth et al. However, the thinly repaired wounds in asthmatic cultures observed in our study are consistent with effective migration without effective regeneration.

The simultaneous resolution of inflammation and resynchronization of epithelial mitotic regeneration on exposure to intermittent glucocorticoids following in vitro injury addresses an important inconsistency in asthma. That is, despite well-demonstrated anti-inflammatory efficacy, inhaled glucocorticoids have not been shown to improve long-term pathologic airway remodeling. The classic model is that asthmatic inflammation leads to long-term pathological lung function decline (i.e. remodeling). However, this is not supported by several trials that have shown inhaled glucocorticoids improve lung function in the short-term but regresses toward the placebo group over the course of several years (Guilbert et al., N Engl J Med 2006, 354:1985-1997; The Childhood Asthma Management Program Research Group, N Engl J Med 2000, 343:1054-1063; Murray et al., Lancet 2006; 368:754-762). Recently, this was confirmed by a large trial comparing inhaled budesonide to placebo in children and adults with recent-onset mild persistent asthma. In this study, the initial pre- and post-bronchodilator differences in fraction of expired volume in 1 second ($FEV_1$) between the treatment and placebo groups disappeared by the fourth year of the study (Busse et al., J Allergy Clin Immunol 2008, 121:1167-1174). Further, asthmatic bronchial biopsy reticular layer thickness does not decrease with inhaled glucocorticoid treatment unless given at relatively high doses (Sont et al., Am J Respir Crit Care Med 1999, 159:1043-1051). These patients were only studied for 2 years so any sustained long-term effect of relatively high dose glucocorticoids remains unclear. Therefore, our data address this inconsistency in asthma by supporting our proposed alternative model of glucocorticoid efficacy in asthma shown in FIG. 5. Therein, direct anti-inflammatory effects of intermittent glucocorticoid dosing are accompanied by simultaneous resynchronization of epithelial mitosis thereby reducing pathological lung remodeling in asthma.

Pulsatile secretion of endogenous adrenal glucocorticoids (i.e. cortisol in humans) can reset an organism's internal and peripheral circadian clocks (Knutsson et al., J Clin Endocrinol Metab 1997, 82:536-540), and this has been shown to occur in the bronchiolar epithelium where it is mediated by Clara cells (Gibbs et al., Endocrinology 2009, 150:268-276). The result of this is synchronous progression of a tissue's cells through normal regeneration/mitosis. The intermittent glucocorticoid exposure scheme used in our experiments was a gross reflection of a circadian peak in circulating endogenous glucocorticoid levels. Although crude by comparison to in vivo glucocorticoid circadian fluctuations, a 2 hour pulse glucocorticoid exposure is sufficient to induce precursors to the inhibition of mitosis, including cyclin-dependent kinase inhibitor $p57^{kiP2}$ (Puddicombe et al., Am J Respir Cell Mol Biol 2003, 28:61-68) and clock gene Per1 (Balsalobre et al., Science 2000, 289:2344-2347).

In summary, these data, generated in an airway model lacking inflammatory cells, support the concept that asthmatic epithelium is intrinsically inflammatory, fibrogenic, and mitotically dyssynchronous. These results support our previously proposed model predicting asthmatic inflammation is driven by intrinsic inflammatory, fibrogenic, and regenerative characteristics of epithelium that are rescued by glucocorticoids (Freishtat et al., Journal of Investigative Medicine 2010, 58:19-22). If extended by further studies, anti-inflammatory treatment of asthma with glucocorticoids may best be redirected to target pathological lung remodeling directly.

Example 2

Figure 5:
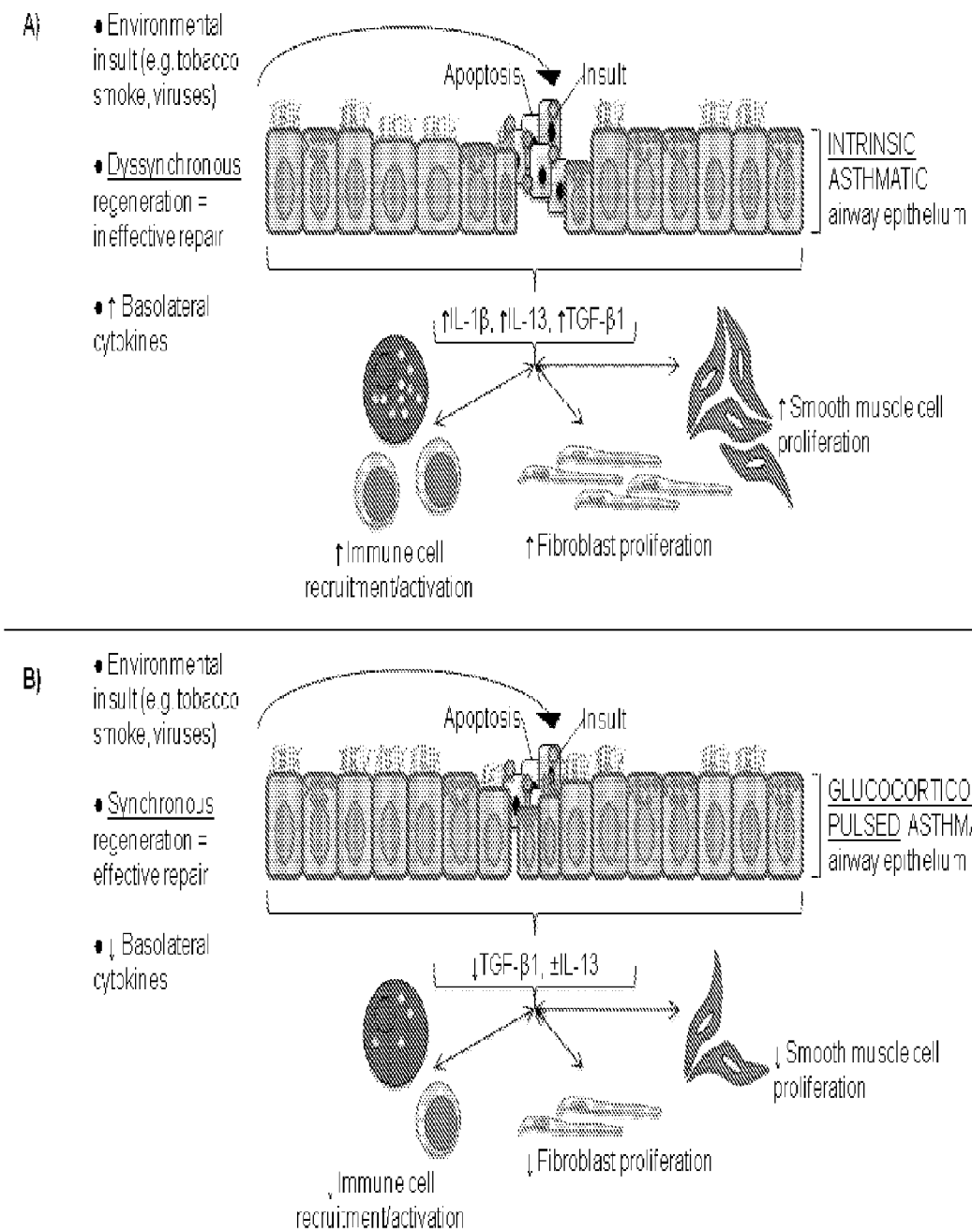
FIG. 5 are charts that show the proposed model for glucocorticoid efficacy in asthma. Tobacco smoke and viruses are among many agents known to induce apoptosis in airway epithelium, prompting regenerative processes. A) Untreated asthmatic airway epithelium is characterized by dyssynchronous regeneration that ineffectively repairs apoptotic regions of epithelium. The concomitant basolateral inflammatory cytokine secretion (e.g. increased IL-1β and TGF-β1, variable IL-10) would lead to pathological immune cell recruitment/activation as well as fibroblast and smooth muscle cell proliferation. B) In our proposed model for glucocorticoid efficacy in asthma, intermittent glucocorticoid dosing simultaneously mediates anti-inflammation in injured asthmatic epithelium and increases the ability of asthmatic epithelium to synchronize its mitosis. This leads to more effective regeneration of injured regions.

Fundamental questions persist about the pathobiology underlying asthma. A prime example of this is the paradigm on which the standard of care for asthma, anti-inflammation with glucocorticoids, is based: chronic asthmatic inflammation is the upstream impetus for long-term airway remodeling (e.g. goblet cell hyperplasia, lung function decline, basement membrane thickening). However, this model is called into question by the persistence of airway remodeling despite effective anti-inflammation with glucocorticoids. To address this inconsistency, we proposed that the principal target of current asthma treatment regimens, inflammation, is actually downstream of the causal biological defect, remodeling (FIG. 5). We showed in Example 1 above that human primary differentiated asthmatic airway epithelial inflammatory cytokine secretions correlate with dyssynchronous mitosis upon in vitro mechanical injury. We show in this example that improving asthmatic airway epithelial cell mitotic cell cycle synchrony reduces inflammatory cytokine secretion.

Materials and Methods

Human fully-differentiated (air-liquid interface) normal (n=3) and asthmatic (n=3) primary airway epithelia, lacking inflammatory cells, were cultured in glucocorticoid-free medium beginning at −48 h. The cells were pulsed with mitotic cell cycle synchrony-inducing (i.e. dexamethasone, simvastatin) compounds or vehicle for 2 h at −26, −2, +22, and +46 h. Cultures were mechanically scrape-wounded at 0 h and thereafter exposed continuously to bromodeoxyuridine (BrdU) to identify mitotically active cells. The time line for the experiment is shown in FIG. 1.

Results

Figure 6:
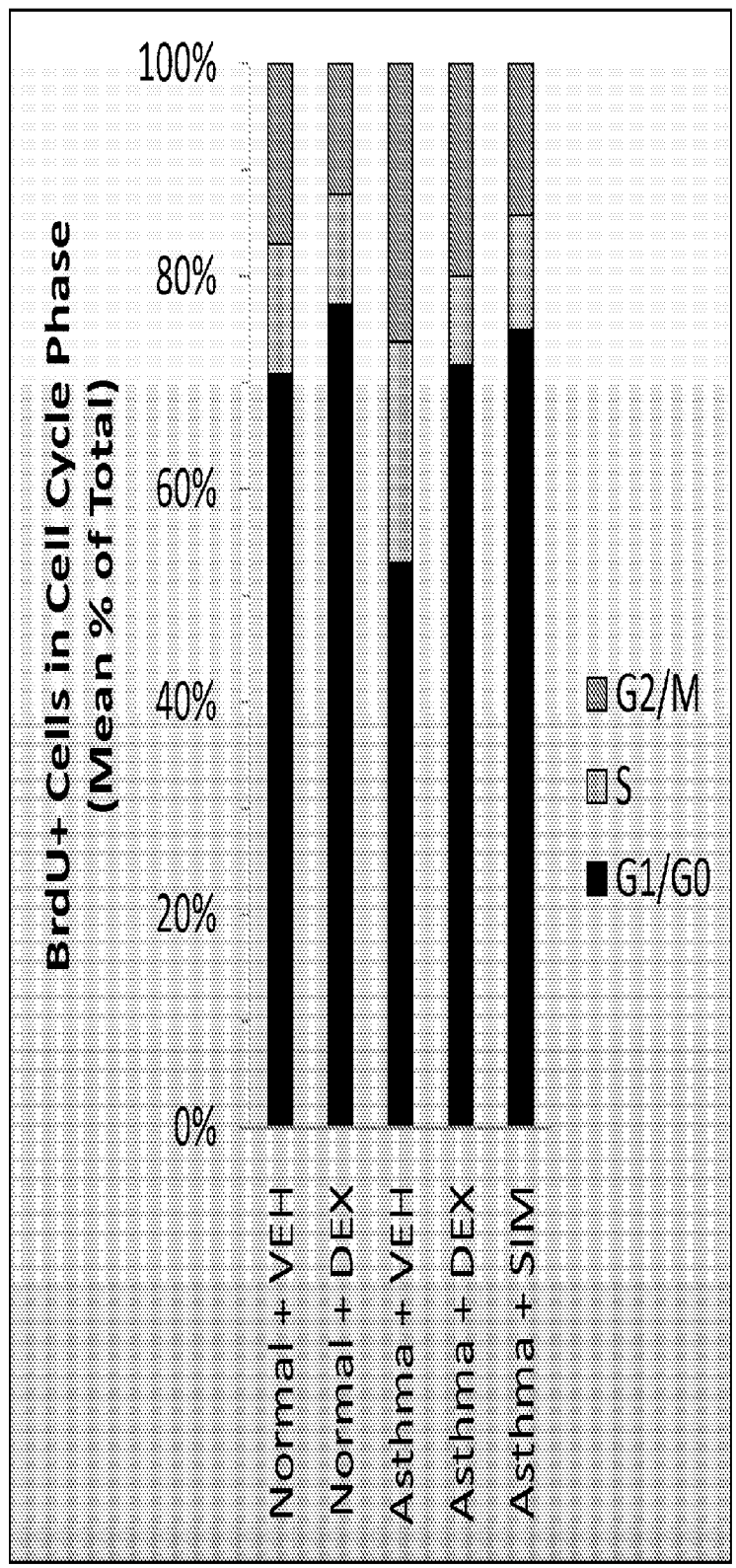
FIG. 6 is a chart that shows that asthmatic epithelial mitosis is dyssynchronous and is improved by both dexamethasone (DEX) and simvastatin (SIM). Cell cycle analysis was performed by flow cytometry of regenerating (i.e. BrdU+) epithelial cells from wounded cultures. Compared to wounded normal epithelia, wounded asthmatic epithelia showed a more even distribution of BrdU+ cells among the cell cycle phases (i.e. G1/G0, S, and G2/M) consistent with mitotic dyssynchrony. Exposure of the asthmatic epithelia to DEX and SIM improved cell cycle synchrony as shown by normalization of the percentage of mitotic cells in each cell cycle phase.
Figure 7:
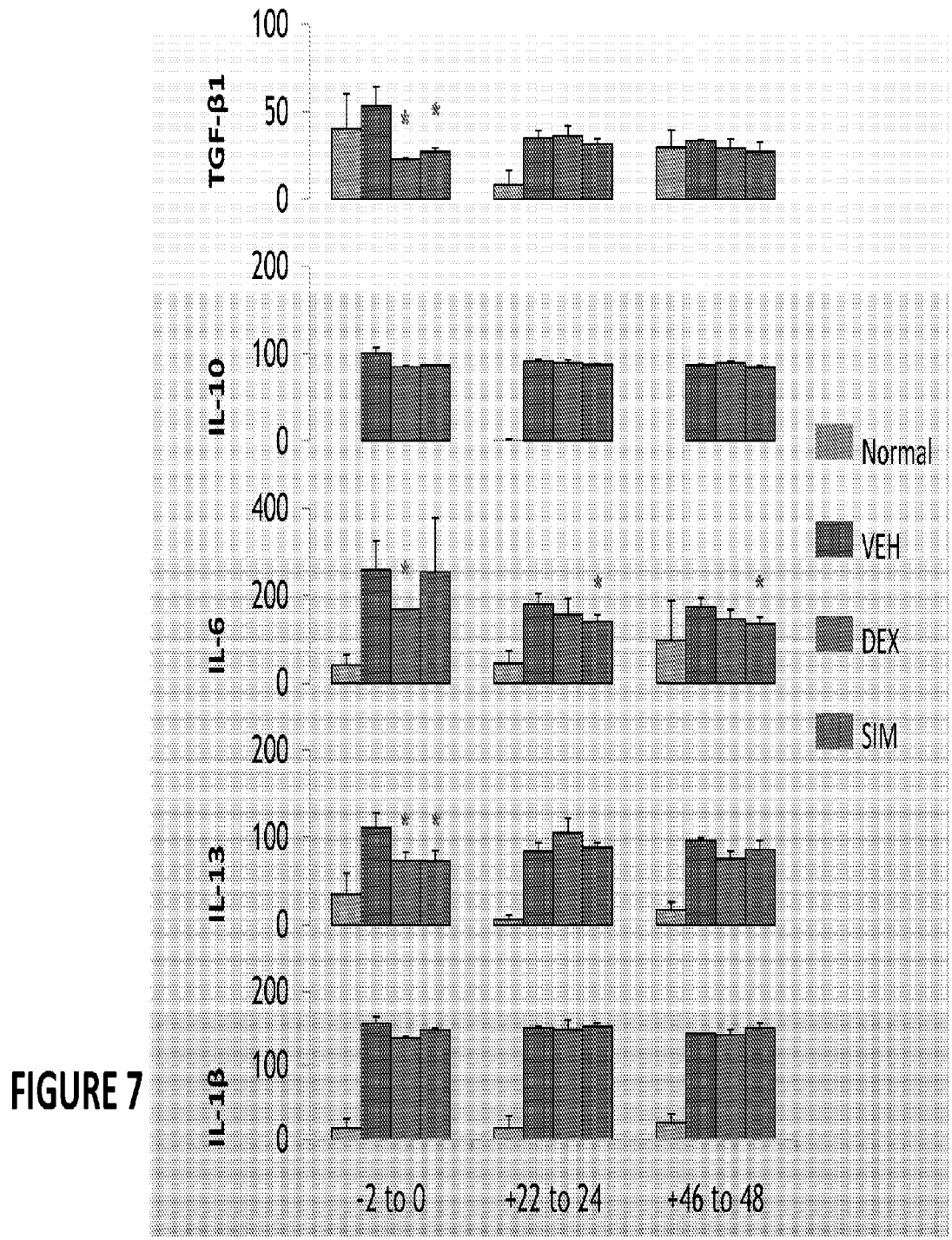
FIG. 7 is a chart that shows that SIM and DEX effectively reduce postwounding asthmatic epithelial basolateral inflammatory secretions. Levels of cytokines measured by cytometric bead assay are shown for basolateral secretions from asthmatic and normal in vitro airway epithelia at 0, +24, and +48 hours. Data are shown as mean±SEM in pg/mL. *P≤0.05 vs. VEH

The results confirmed our previous findings, discussed in Example 1, that asthmatic epithelia secreted more basolateral cytokines and regenerated less efficiently than normals following wounding (FIG. 6). Asthmatic epithelia were dyssynchronously distributed along the cell cycle (G1/G0, S, G2/M: 52±10, 25±4, 23±7%) compared to normal epithelia (71±1, 12±2, 17±2%) (FIG. 6). Dexamethasone pulses improved mitotic cell cycle synchrony (72±5, 8±2, 20±4%) (FIG. 6) while reducing asthmatic epithelial inflammatory cytokine secretion (FIG. 7). Similarly, simvastatin improved asthmatic epithelial mitotic cell cycle synchrony (75±6, 11±4, 14±3%) (FIG. 6) and reduced basolateral TGFB1, IL-6, and IL-13 secretion ($0.01 < P < 0.04$) (FIG. 7).

Although certain presently preferred embodiments of the invention have been specifically described herein, it will be apparent to those skilled in the art to which the invention pertains that variations and modifications of the various embodiments shown and described herein may be made without departing from the spirit and scope of the invention. Accordingly, it is intended that the invention be limited only to the extent required by the appended claims and the applicable rules of law.

What is claimed is:

1. A method for monitoring a treatment efficacy of an individual with asthma comprising the steps of:
   a. administering a candidate compound to an individual;
   b. obtaining a cell sample of an individual's airway epithelium;
   c. inducing the cells to undergo mitosis; and
   d. determining the synchrony of the mitotic cells, wherein the candidate compound is effective in the treatment of asthma if the cells become more synchronous after the administration of the candidate compound.

2. The method of claim 1, further comprising the step of determining the release of inflammatory cytokines by the cells.

3. The method of claim 1, wherein the candidate compound is selected from the group consisting of proteins, peptides, small molecules, vitamin derivatives, and carbohydrates.

* * * * *